US008263067B2

(12) United States Patent
Holm (10) Patent No.: US 8,263,067 B2
(45) Date of Patent: Sep. 11, 2012

(54) ADENOVIRAL SYSTEMS AND THE USES THEREOF

(76) Inventor: Per Sonne Holm, Furstenfeldbruck (DK)

( * ) Notice: Subject to any disclaimer, the term of this patent is extended or adjusted under 35 U.S.C. 154(b) by 576 days.

(21) Appl. No.: 10/451,210

(22) PCT Filed: Dec. 21, 2001

(86) PCT No.: PCT/EP01/15212
§ 371 (c)(1),
(2), (4) Date: Nov. 17, 2003

(87) PCT Pub. No.: WO02/053711
PCT Pub. Date: Jul. 11, 2002

(65) Prior Publication Data
US 2004/0067586 A1    Apr. 8, 2004

(30) Foreign Application Priority Data

Dec. 28, 2000 (DE) .................................. 100 65 504
Oct. 16, 2001 (DE) .................................. 101 50 945

(51) Int. Cl.
*C12N 15/00* (2006.01)
*C12N 15/09* (2006.01)
*C12N 15/12* (2006.01)
*C12N 15/34* (2006.01)

(52) U.S. Cl. ................... 424/93.2; 435/320.1; 435/69.1; 536/23.1; 536/24.1

(58) Field of Classification Search .......................... None
See application file for complete search history.

(56) References Cited

U.S. PATENT DOCUMENTS

| 5,856,181 | A | | 1/1999 | McCormick |
| 5,871,726 | A | | 2/1999 | Henderson et al. |
| 6,022,863 | A | * | 2/2000 | Peyman ....................... 514/44 R |
| 6,110,744 | A | | 8/2000 | Fang et al. |
| 6,140,126 | A | | 10/2000 | Bennett et al. |
| 2002/0091083 | A1 | * | 7/2002 | Higashi et al. .................. 514/12 |
| 2003/0044383 | A1 | * | 3/2003 | Henderson et al. ........... 424/93.2 |
| 2003/0095989 | A1 | * | 5/2003 | Irving et al. ................ 424/233.1 |

FOREIGN PATENT DOCUMENTS

| DE | 199 29 569 A1 | 6/1999 |
| DE | 101 31 122 A1 | 6/2000 |
| WO | WO 99/06576 | 2/1999 |
| WO | WO 00/39317 | 7/2000 |
| WO | WO 00/56909 | 9/2000 |

OTHER PUBLICATIONS

Ting et al, YB-1 DNA-binding Protein Represses Interferon Activation of Class II Major Histocompatibility Complex Genes, J. Exp. Med, vol. 179 May 1994; 1605-1611.*
Kozarsky and Wilson, Gene Therapy: Adenovirus Vectors, 1993, Current Opinions in Genetics and Development, pp. 499-503.*
Koike et al., FEBS Letter 417 (1997) 390-394 "Nuclear translocation of the Y-box binding protein by ultraviolet irradiation".
Yun at al., Journ. Of Biological Chemistry vol. 274, No. 42, Issue of Oct. 15, pp. 29677-29682, 1999 "p53 Negatively Regulates cdc2 Transcription via the CCCAT-binding NF-Y Transription Factor".
Safak at al., Journal of Virology, Dec. 1999, p. 10146-10157 "Physical and Functional Interaction between the Y-Box Bdingin Protein YB-1 and Human Polyomavirus JC Virus Large T Antigen".
Kim et al., Cancer Gene Therapy, vol. 5; No. 6, 1998 "Adenovirus E1A mutants that selectively replicate in and cause enhanced destruction of cancer cells in vitro and in nude mouse-human tumor xenografts".
Heise at al., Nature Medicine, vol. 3, No. 6, Jun. 1997 "ONYX-015, an E1B gene-attenuated adenovirus, causes tumor-specific cytolysis and antitumoral efficacy that can be augmented by standard chemotherapeutic agents".
Bargou et al., Nature Medicine, vol. 3, No. 4, Apr. 1997 "Nuclear localization and increased levels of transcription factor YB-1 in primary human breast cancers are associated with intrinsic MDR1 gene expression".
Rittner, at al., Journal of Virology, Apr. 1997, p. 3307-3311, vol. 71, No. 4 "Conditional Repression of the E2 Transcription Unit in E1-E3 Deleted Adenovirus Vectors is Correlated with a Strong Reduction in Viral DNA Replication and Late Gene Expression in Vitro".
Fang et al, Journal of Virology, Jun. 1997, p. 4798-4803, vol. 71, No. 6 "Diminishing Adenovirus Gene Expression and Viral Replication by Promoter Replacement".

* cited by examiner

*Primary Examiner* — Maria Marvich
(74) *Attorney, Agent, or Firm* — Lisa V. Mueller; Michael Best & Friedrich LLP (57) ABSTRACT

The invention is related to a nucleic acid comprising an adenoviral nucleic acid, which also comprises a nucleic acid sequence coding for YB-1.

7 Claims, 3 Drawing Sheets

ADENOVIRAL SYSTEMS AND THE USES THEREOF

The present invention is related to nucleic acids comprising adenoviral nucleic acid, adenoviruses comprising these nucleic acids and the use thereof.

Numerous therapeutical plans are at present used to treat tumours. In addition to the use of surgical techniques, chemotherapy and radiation therapy are mainly used. However, all these methods are associated with considerable side-effects for the patient.

The use of replication-selective oncolytic viruses has created a new platform for treating tumours. In this method a selective intratumoural replication of a viral agent is induced which results in virus replication, lysis of the infected tumour cell and spread of the virus to the neighbouring tumour cells. Since the virus is only able to replicate in tumour cells, normal tissue is protected from infection by the virus and thus from viral lysis. Examples of such replication-selective oncolytic viruses are gene attenuated adenovirus and herpes viruses (Martuza, R. et al. Science 252, 854-858 (1991); Fueyo, J. et al. Oncogene 19, 2-12 (2000)).

An example of such an adenovirus is dl 1520 (Onyx-015) which has already been successfully used in clinical phases I and II (Khuri, F. et al. Nature Medicine 6, 879-885 (2000)). Onyx-015 is an adenovirus in which the E1B 55 kDa gene is deleted. The E1B 55 kDa gene product is involved in the inhibition of p53, the transport of viral mRNA and switching off protein synthesis of the host cell. In this connection p53 is inhibited by formation of a complex consisting of p53 and the E1B 55 kDa protein coded by the adenovirus. P53 which is coded by TP53 is the basis for a complex regulatory mechanism (Zambetti, G. P. et al., FASEB J. 7, 855-865) which, among others, results in suppression of the efficient replication of viruses such as adenoviruses in the cell. The gene TP53 is deleted or mutated in about 50% of all human tumours and consequently the desired apoptosis does not occur as a result of chemotherapy or radiation therapy and thus these tumour treatments are usually unsuccessful.

DNA tumour viruses such as adenoviruses drive the infected cells into the S phase of the cell cycle in order to facilitate viral DNA replication. Onyx-015 does not express the E1B 55 kDa protein and replicates selectively in tumour cells but not in normal cells. Furthermore another selectivity is that tumours that are deficient in p53 are necrosed by the viral lysis of the tumour cells to a greater extent than those tumours which have the p53 wild-type (Khuri et al., loc.cit.). Despite the fundamental effectiveness of Onyx-015 in viral-induced oncolysis in the case of p53-deficient tumours, the success rate of 15% of treated tumours is very low.

Ries et al. (Ries, S. J. et al. Nature Medicine 6, 1128-1132 (2000)) have described a basic approach for successfully using Onyx-015 even for tumours with the p53 wild-type. In this case the tumour suppressor protein p14ARF is not expressed. As a result of the absence of p14ARF the normal reaction of the p53 system to a viral infection does not take place and thus allows Onyx-015 to also replicate in these tumours. However, an application of this finding requires that there is a suitable genetic background in the tumour cell or that such a background is provided by suitable therapeutic measures. In the former case this would further reduce the number of tumours that can be treated by Onyx-015 and in the latter case it would require a complicated change in the genetic background of the tumour cells.

It is an object of the present invention to improve the existing adenoviral systems for viral-induced oncolysis. In particular the aim is to increase the success rate of tumour treatment compared with the prior art.

Another object of the present invention is to provide adenoviral systems for viral-induced oncolysis which are also effective on tumours that are of the p53 wild-type.

According to the invention the object is achieved in a first aspect by a nucleic acid comprising an adenoviral nucleic acid wherein the nucleic acid comprises a nucleic acid sequencing coding for YB-1.

One embodiment provides that the adenoviral nucleic acid comprises a nucleic acid coding for E1-B.

Another embodiment provides that the adenoviral nucleic acid comprises a nucleic acid coding for E4orf6.

In yet another embodiment a promoter is provided which controls the expression of E1-B.

In another embodiment a promoter is provided which controls the expression of E4orf6.

Another embodiment provides that E1B is the E1-B 55 kDa protein.

Another embodiment provides that the nucleic acid codes for functionally inactive gene products E1B and/or E1 and/or E3 and/or E4.

In a second aspect the object is achieved by a nucleic acid comprising a nucleic acid sequence coding for YB-1 and a nucleic acid sequence mediating a nuclear transport of YB-1.

Another embodiment provides that the nucleic acid sequence mediating the nuclear transport of YB-1 is selected from the group comprising signal sequences and transport sequences.

A third aspect of the invention is related to a nucleic acid comprising an adenoviral nucleic acid wherein the adenoviral nucleic acid comprises a tumour-specific promoter instead of a or the functional E2 late promoter, in particular the functionally active E2 late promoter.

A fourth aspect of the invention concerns a nucleic acid comprising an adenoviral nucleic acid wherein the adenoviral nucleic acid comprises a tissue-specific promoter instead of a or the functional E2 late promoter, in particular the functionally active E2 late promoter.

The object is achieved in a fifth aspect by an adenoviral replication system comprising an adenoviral nucleic acid, whereby the adenoviral nucleic acid is deficient for the expression of the E1A protein, and comprising a nucleic acid of a helper virus, whereby the nucleic acid of the helper virus comprises a nucleic acid sequence which codes for YB-1.

One embodiment provides that the adenoviral nucleic acid and/or the nucleic acid of the helper virus is present as a replicable vector.

The object is achieved in a sixth aspect by a vector, preferably an expression vector, which comprises one of the nucleic acids according to the present invention.

The object is achieved in a seventh aspect by a group of vectors comprising of at least two vectors, whereby the overall vector group contains an adenoviral replication system according to the present invention.

One embodiment provides that each component of the adenoviral replication system is located on a suitable vector, preferably an expression vector.

Another embodiment provides that at least two components of the adenoviral replication system are located on a vector of the group of vectors.

An eighth aspect of the invention is related to an adenovirus comprising one of the nucleic acids according to the present invention.

One embodiment provides that the adenovirus comprises a capsid.

A ninth aspect of the invention is related to a cell comprising a nucleic acid according to the present invention and/or an adenoviral replication system according to the present invention and/or a vector according to the present invention and/or a group of vectors according to the present invention and/or an adenovirus according to the present invention.

A tenth aspect of the invention is related to the use of a nucleic acid according to the present invention and/or an adenoviral replication system according to the present invention and/or a vector according to the present invention and/or a group of vectors according to the present invention and/or an adenovirus according to the present invention and/or a cell according to the present invention for the manufacture of a medicament.

One embodiment provides that the medicament is used for the treatment and/or prophylaxis of tumour diseases.

In yet another embodiment the medicament additionally comprises a pharmaceutically effective compound.

One embodiment provides that the pharmaceutically effective compound is selected from the group comprising cytostatic agents. Suitable cytostatic agents are among others cis-platinum, Taxol, Daunoblastin, Adriamycin and Mitoxantron.

An eleventh aspect of the invention is related to the use of a nucleic acid according to the present invention and/or an adenoviral replication system according to the present invention and/or a vector according to the present invention and/or a group of vectors according to the present invention and/or an adenovirus according to the present invention and/or a cell according to the present invention for the manufacture of a medicament for the treatment and/or prophylaxis of tumour diseases, whereby YB-1 is located in the nucleus of the tumour cells independent of the cell cycle.

One embodiment provides that the nucleic acid codes for an adenoviral nucleic acid and that the adenoviral nucleic acid is E1B-deficient, and in particular E1B 55 kDa-deficient.

Another embodiment provides that the adenovirus is E1B-deficient, and in particular E1B 55 kDa-deficient.

An alternative embodiment provides that the nucleic acid codes for an adenoviral nucleic acid and that the adenoviral nucleic acid codes for E1B, and in particular for E1B 55 kDa.

One embodiment provides that the adenovirus expresses E1B, and in particular EB 55 kDa.

Yet a further embodiment provides that the adenoviral nucleic acid codes for E1A.

Yet another embodiment provides that the adenovirus expresses E1A.

In the various embodiments the tumour and/or the tumour disease is selected from the group comprising p53-positive tumours, p53-negative tumours, malignant tumours, benign tumours and combinations thereof.

A twelfth aspect of the invention is related to a method for the screening of patients which can be treated with an E1B-deficient, preferably E1B 55 kDa-deficient adenovirus which comprises the following steps:
  examining a sample of the tumour tissue and
  determining whether YB-1 is located in the nucleus independently of the cell cycle.

One embodiment provides that the tumour tissue is examined using an agent which is selected from the group comprising antibodies against YB-1.

A thirteenth aspect of the invention is related to the use of an antibody against YB-1 to determine which patients, in particular which tumour patients can be treated with an E1B-deficient adenovirus, preferably an E1B 55 kDa-deficient adenovirus.

A fourteenth aspect of the invention is related to a complex comprising at least one YB-1 molecule and at least one E1B 55 kDa protein.

One embodiment provides that the YB-1 molecule is a transgenic YB-1 molecule.

Another embodiment provides that the YB-1 is YB-1 expressed in the nucleus.

In connection with the nucleic acids disclosed herein, the term is also used in the sense of nucleic acid sequences. The nucleic acids according to the present invention and the adenoviruses according to the present invention are preferably recombinant products especially when they have been changed compared to the wild-type. In the context of the present invention the nucleic acids according to the present invention and the adenoviruses according to the present invention typically have an E1 deletion, an E1-E3 deletion and/or an E4 deletion i.e. the nucleic acid or the corresponding adenoviruses are not able to produce functionally active E1 and/or E3 and/or E4 expression products or such products cannot be produced from them. This is typically achieved by a deletion or an appropriate mutation, including a point mutation.

A fifteenth aspect of the present invention is related to the use of a complex comprising at least one YB-1 molecule and at least one E1A protein.

One embodiment provides that one or more of the proteins of the E1A region have a transactivating effect on adenoviral gene expression but does/do not activate the replication of an adenovirus.

A sixteenth aspect of the invention is related to the use of a complex according to the present invention comprising at least one YB-1 molecule and at least one E1A protein, for treating tumours, and in particular for tumour lysis.

A seventeenth aspect of the present invention is related to the use of an E1B-deficient adenovirus for the manufacture of a medicament for treating tumours which have YB-1 in the nucleus.

A preferred embodiment provides that the nuclear localization of YB-1 is achieved under the influence of exogenous measures.

A particularly preferred embodiment provides that the exogenous measures are measures which are selected from the group comprising irradiation, cytostatic agents and hyperthermia.

Yet a further aspect of the invention provides that the exogenous measure is used on the organism for which the medicament is to be used.

Other embodiments are derived from the subclaims.

The present invention is based on the surprising finding that after infection of a cell and typically of a tumour cell with an adenovirus a complex is formed between YB-1 and the adenoviral gene product E1B-55 kDa and this complex formation results in a transport of YB-1 into the nucleus which allows an effective replication of the virus in the cell nucleus in vivo. It was also found that E4orf6 also binds to E1B-55 K (Weigel, S., Dobbelstein, M. J. Virology, 74, 764-772, 2000). The nuclear export signal within the E4orf6 protein of adenovirus type 5 supports virus replication and cytoplasmic accumulation of viral mRNA; (Keith N. Leppard, Seminars in Virology, 8, 301-307, 1998. Regulated RNA processing and RNA transport during adenovirus infection) and thus mediates transport or distribution of E1B-55 K in the nucleus. Hence the interaction between E1B-55 K and YB-1 or E1B-55 K, YB-1 and E4orf6 results in an efficient replication of the virus which in turn leads to a lysis of the cell, release of the virus and infection and lysis of neighbouring cells so that if a tumour cell or a tumour is infected, the tumour is ultimately lysed, i.e. an oncolysis occurs.

Another finding on which the present invention is based, is that YB-1 binds as a transcription factor to the late E2 promoter of adenovirus and as a result activates the replication of the adenovirus. This provides new adenoviruses and adenoviral systems for oncolysis.

The present invention is also based on the surprising finding that the expression of the transgene YB-1 in an adenoviral vector leads to viral replication. The viral genes E1B, E3 and E4 are not switched on in this process which is mainly due to the fact that E1 and/or E3 are deleted in the adenoviral vector. However, these genes are necessary for a very efficient replication and particle formation (Goodrum, F. D., Omelles, D. A. Roles for the E4orf6, orf3 and E1B 55-kilodalton proteins in cell cycle-independent adenovirus replication. J. Virol. 73, 74474-7488 (1999); Medghalchi, S., Padmanabhan, R., Ketner, G. Early region 4 modulates adenovirus DNA replication by two genetically separable mechanisms. Virology, 236, 8-17 (1997). It is also known that two proteins (the 12S and the 13S protein) which are coded by E1A, control and induce the expression of other adenoviral genes (Nevins, J. R. Mechanism of activation of early viral transcription by the adenovirus E1A gene products. Cell 26, 213-220 (1981); Boulanger, P et al. (1991); Biochem. J. 275, 281-299). It has been shown that the CR3 region of the 13S protein is mainly responsible for the transactivating function (Wong H K, Ziff E B. Complementary functions of E1a conserved region 1 cooperate with conserved region 3 to activate adenovirus serotype 5 early promoters. J. Virol. 1994, 68(8): 4910-20). Adenoviruses with certain deletions in the CR1 and/or CR2 region of the 13S protein cannot replicate but still have a transactivating effect on the viral genes and promoters (Wong H K, Ziff E B. Complementary functions of E1a conserved region 1 cooperate with conserved region 3 to activate adenovirus serotype 5 early promoters. J. Virol. 1994, 69(8): 4910-20).

A combination of such a system, i.e. a system which switches on the viral genes but is not capable of viral replication, with a tumour or tissue-specific expression of the transgene YB-1 would, in contrast, allow a very effective viral replication or particle formation and thus oncolysis. Any of the promoters that have been described herein anywhere can be used as suitable tumour-specific or tissue-specific promoters.

YB-1 is a representative of the Y box protein family which binds to the DNA Y box sequence motif. The Y box motif is a transcriptional regulatory element which is found in the promoter or enhancer regions of a number of different genes which play a role in the regulation of cell proliferation (Ladomery, M. et al., 1995; Bioassays 17:9-11; Didier, D. K. et al., 1988, PNAS, 85, 7322-7326).

Figure 1:
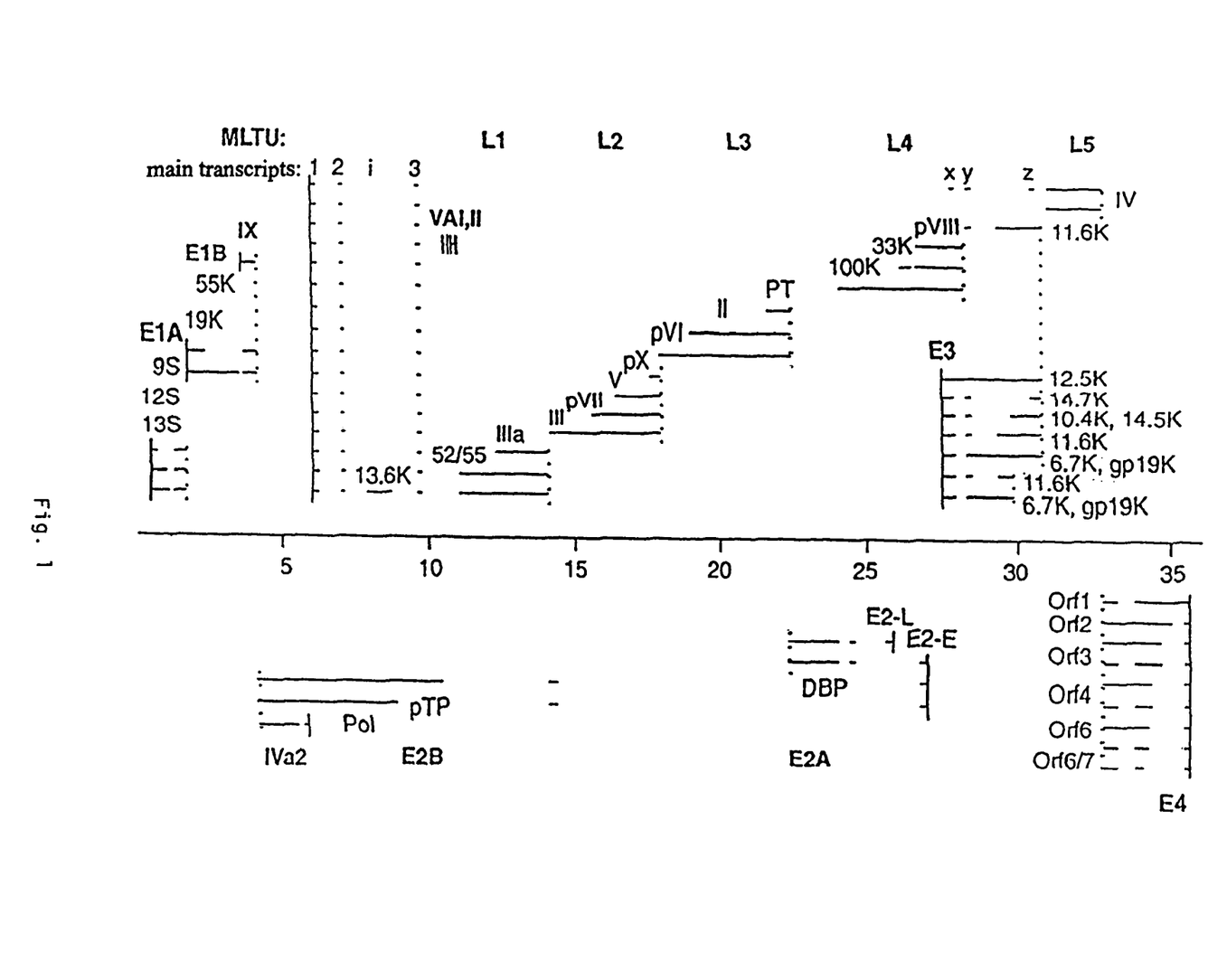
FIG. 1 shows the basic molecular-genetic organization of the adenovirus.

Adenoviruses are known in the prior art. They are dsDNA viruses (Boulanger, P. et al. (1991); Biochem. J. 275, 281-299). The organization of the genome is shown in FIG. 1. The complete nucleotide sequence of the adenoviral genome is known and is described in Chroboczek, J. et al. (Chroboczek, J. et al., Virology 1992, 186, 280-285). A part of the genome which is particularly important for the application of adenoviruses are the so-called early genes and their gene products which are referred to as E1, E2, E3 and E4. E1 consists of two gene products E1A and E1B which represent oncogenes. The total of three gene products of the E2 group are involved in replication together with the gene products E3 and E4.

The adenoviral systems known in the prior art for oncolysis such as Onyx-015 have an E1B-55 kDa protein deletion. This deletion was made under the assumption that an intact p53 gene counteracts an efficient replication in vivo and in order to ensure an adenoviral replication in vivo only in p53-negative/mutated cells, but results in a reduction by two orders of magnitude in the particle number compared to the wild-type as a result of impaired replication. On the other hand these adenoviral systems of the prior art rely on E1A in order to control in vivo replication mediated by the E2 early promoter.

The present invention differs from this principle in that the adenoviral systems described herein are based on the E2 late promoter.

Within the scope of the present invention the terms adenovirus and adenoviral systems are to be understood as having essentially the same meaning. Adenovirus is to be understood especially as the complete virus particle containing the capsid and nucleic acid. The term adenoviral system indicates in particular that the nucleic acid is changed compared to the wild-type. Such changes preferably comprise changes in the structure of the genome of the adenovirus such as the deletion and/or addition and/or mutation of promoters, regulatory sequences and coding sequences (such as the reading frame). The term adenoviral systems is also preferably used in the context of a vector.

The adenoviral nucleic acids to which reference is made herein, are known in the prior art. A person skilled in this field will know how to delete or mutate the adenoviral nucleic acid sequences that are unimportant for the invention. Such deletions can for example affect the nucleic acid coding for E3. In preferred embodiments these adenoviral nucleic acids can still be packaged in the viral capsid and thus form infectious particles. The same applies to the nucleic acids according to the present invention. In general it should also be noted that the adenoviral systems can be deficient with regard to one or more expression products. It should be taken into consideration that this may be due to the fact that the nucleic acid coding for the expression product is mutated or deleted completely or to such an extent that essentially no more expression product is formed or that the regulatory elements or the elements controlling expression such as promoters or transcription factors, are absent whether at a nucleic acid level (absence of a promoter; cis-acting element) or at the level of the translation or transcription system (trans-acting elements). In particular the latter aspect may depend on the respective cellular background.

The nucleic acid according to the present invention which comprises an adenoviral nucleic acid and additionally a nucleic acid sequence coding for YB-1, is preferably a recombinant nucleic acid. In this context the reading frame for the nucleic acid coding for YB-1 may be under the control of an element controlling expression and/or translation. This may for example be an adenoviral promoter or a non-adenoviral promoter. Suitable non-adenoviral promoters can be selected from the group comprising cytomegalovirus promoter, RSV (Rous sarcoma virus) promoter, adenovirus-based promoter Va I and a non-viral YB-1 promoter. Other viral promoters which can be used in connection with any aspects of the invention disclosed herein are the telomerase promoter, the alpha fetoprotein (AFP) promoter, the carcinoembryonic antigen promoter (CEA) (Cao, G., Kuriyama, S., Gao, J., Mitoro, A., Cui, L., Nakatani, T., Zhang, X., Kikukawa, M., Pan, X., Fukui, H., Qi, Z. Comparison of carcinoembryonic antigen promoter regions isolated from human colorectal carcinoma and normal adjacent mucosa to induce strong tumour-selective gene expression. Int. J. Cancer, 78, 242-247, 1998), the L-plastin promoter (Chung, I., Schwartz, PE., Crystal, RC., Pizzomo, G. Leavitt, J., Deisseroth, AB. Use of L-plastin promoter to develop an adenoviral system that confers transgene expression in ovarian cancer cells but not in normal mesothelial cells. Cancer Gene Therapy, 6, 99-106, 1999), arginine-vasopressin promoter (Coulson, J M, Staley, J., Woll, P J. Tumour-specific arginine vasopressin promoter activation in small cell lung cancer. British J. Cancer, 80, 1935-1944, 1999) and the PSA promoter (Hallenbeck P L, Chang, Y N, Hay, C. Golightly, D., Stewart, D., Lin, J., Phipps, S., Chiang, Y L. A novel tumour-specific replication-restricted adenoviral vector for gene therapy of hepatocellular carcinoma. Human Gene Therapy, 10, 1721-1733, 1999).

It is known that the telomerase promoter is of pivotal importance in human cells. Thus telomerase activity is regulated by the transcriptional control of the telomerase reverse transcriptase gene (hTERT) which represents the catalytic subunit of the enzyme. Telomerase expression is active in 85% of human tumour cells. In contrast it is inactive in most normal cells. Exceptions are germ cells and embryonic tissue [Braunstein, I. et al. (2001). Human telomerase reverse transcription promoter regulation in normal and malignant human ovarian epithelial cells. Cancer Research, 61, 5529-5536; Majumdar A S et al. (2001). The telomerase reverse transcriptase promoter drives efficacious tumour suicide gene therapy while preventing hepatotoxicity encountered with constitutive promoters. Gene Therapy, 8, 568-578]. Detailed examinations of the hTERT promoter have shown that fragments of the promoter at a distance of 283 bp and 82 bp from the initiation codon are sufficient for a specific expression in tumour cells (Braunstein, I. et al.; Majumdar A S et al., loc.cit.). Hence this promoter and the specific fragments are suitable for achieving a specific expression of a transgene only in tumour cells. The promoter should enable the expression of the transgene YB-1 and/or a truncated form which is still functionally active only in tumour cells. The expression of the transgene in an adenoviral vector then leads to viral replication of the adenoviral vector and consequently to oncolysis. It is also within the scope of the present invention that the reading frame of YB-1 is in frame with one or more of the gene products of the adenoviral system. However, the reading frame of YB-1 may also be independent thereof. The nucleic acid coding for YB-1 can be a complete sequence. However, it is also possible within the scope of the present invention that the nucleic acid sequence is truncated. Such a truncated nucleic acid sequence and also such a truncated YB-1 protein is especially within the scope of the present invention when such a truncated YB-1 still has a function or property like that of the complete YB-1. Such a function or property is for example the ability to enter the nucleus, with or without binding to the E1B-55 kDa protein, or to bind to the E2 late promoter.

The adenoviral nucleic acid which is comprised in the nucleic acid according to the present invention can be any adenoviral nucleic acid which itself leads to a replication event or leads to such a replication event in conjunction with other nucleic acid sequences. The other nucleic acid sequences can for example be YB-1. As elucidated below it is possible in this context that the sequences and/or gene products required for replication are provided by helper viruses. An example of such an adenoviral nucleic acid is the nucleic acid of Onyx-015 which allows expression of E1A but not of E1B.

In the embodiment of the nucleic acid according to the present invention which comprises a nucleic acid sequence coding for YB-1, the adenoviral nucleic acid may comprise a nucleic acid coding for E1-B. In this context it is possible that although the nucleic acid coding for E1-B is present, the E1-B which it encodes, is not expressed. This can for example be achieved when the nucleic acid coding for E1-B lacks a suitable promoter. This is for example the case when E1A is not expressed. However, it is also within the scope of the present invention that E1-B is expressed, for example when the nucleic acid coding for E1-B is under the control of a suitable promoter. A suitable promoter is for example selected from the group comprising the cytomegalovirus promoter, RSV (Rous sarcoma virus) promoter, adenovirus-based promoter Va I and the non-viral YB-1 promoter. Moreover, the above-mentioned promoters are also suitable in this case, i.e. the telomerase promoter, the alpha fetoprotein (AFP) promoter, the carcinoembryonic antigen promoter (CEA), the L-plastin promoter, the arginine-vasopressin promoter and the PSA promoter.

As disclosed herein E1-B-55 k is involved in the distribution and the transport of YB-1 in the cell nucleus. Since E4orf6 in turn binds to E1-B-55 k and is also responsible for the transport of E1-B-55 into the nucleus, E4orf6 also plays an important role in the distribution and transport of YB-1 into the cell nucleus. Hence it is also within the scope of the present invention that the genes of the E4 region, and in particular E4orf6, are also under the control of one of the promoters mentioned above. In this context a preferred embodiment provides that the adenoviral E4 promoter is no longer functional. It is particularly preferred when the adenoviral E4 promoter is deleted.

One embodiment of the nucleic acid according to the present invention which comprises a nucleic acid sequence coding for YB-1, provides that the adenoviral nucleic acid comprises a nucleic acid coding for E1-A but that the adenoviral nucleic acid does not allow expression of E1-B and thus corresponds to the structure of the DNA of Onyx-015.

In general when reference is made herein to E1-B it preferably applies to the E1 B 55 kDa protein unless stated otherwise.

If reference is made herein to coding nucleic acid sequences and these are nucleic acid sequences that are known, it is within the scope of the invention to not only use an identical sequence but also sequences that are derived therefrom. Derived sequences are understood herein especially as sequences which still result in a gene product which has a function that corresponds to a function of the non-derived sequence. This can be ascertained by simple routine tests. An example of such derived nucleic acid sequences are nucleic acid sequences which code for the same gene product in particular for the same amino acid sequence, but have a different base sequence as a result of the degeneracy of the genetic code.

Another aspect of the nucleic acid according to the present invention comprising a nucleic acid coding for YB-1 and a nucleic acid sequence mediating transport of YB-1 into the nucleus, is based on the surprising finding that when YB-1 is present in the nucleus, especially independent of the cell cycle, an adenoviral replication occurs in the cell, preferably in a tumour cell. In connection therewith the nucleic acids, adenoviruses and adenoviral systems each according to the present invention can be used as such or in combination with the adenoviruses known in the art such as Onyx-015, as adenoviruses and adenoviral systems, respectively, and the corresponding nucleic acids therewith.

Suitable nucleic acid sequences for mediating nuclear transport are known to the ones skilled in the art and are described for example in (Whittaker, G. R. et al., Virology, 246, 1-23, 1998; Friedberg, E. C., TIBS 17, 347 1992; Jans, D. A. et al. Bioessays 2000 June; 22(6): 532-44; Yoneda, Y., J. Biochem. (Tokyo) 1997 May; 121(5): 811-7; Boulikas, T., Crit. Rev. Eukaryot. Gene Expr. 1993; 3(3): 193-227). Different mechanisms can be used by the nucleic acid sequences mediating nuclear transport. One of these mechanisms is that YB-1 is formed as a fusion protein with a signal peptide and because of the signal peptide YB-1 is transported into the cell nucleus. Another mechanism is that YB-1 is provided with a transport sequence which results in YB-1 being transported into the cell nucleus where it promotes viral replication preferably after it has been synthesized in the cytoplasm. An example of a nucleic acid sequence that is particularly effective in mediating transport into the nucleus is the TAT sequence of HIV which, in addition to other suitable nucleic acid sequences of this type, is described for example in Efthymiadis, A., Briggs, L J, Jans, D A. The HIV-1 tat nuclear localisation sequence confers novel nuclear import properties. JBC, 273, 1623.

Another aspect of the invention comprising a nucleic acid comprising an adenoviral nucleic acid whereby the adenoviral nucleic acid comprises a tumour-specific promoter instead of the E2 late promoter, is also based on the surprising finding that the expression and hence the replication of the adenovirus and thus oncolysis depends essentially on the control of the adenoviral genes and gene products, in particular in the E2 region by the E2 late promoter, especially in vivo. The E2 region of adenovirus which represents a transcription unit, is composed of the E2A and E2B genes which code for proteins that are vital for viral replication: pTP (precursor terminal protein), DNA polymerase and DBP which is a multifunctional DNA binding protein. Within the scope of the present invention the terms deleted promoter, non-functionally active, functionally non-active or non-functional promoter mean that the promoter as such is no longer active, i.e. no longer results in transcription. Such a non-functional promoter can be generated by known methods by a person skilled in this art. For example this can be accomplished by a complete deletion of the promoter, by a partial deletion of the promoter or by a point mutation. Other methods of mutating such promoters are, for example, to change the spatial relationship between the elements of which the promoter is composed resulting in a functional inactivation.

The inactivation of the E2 late promoter and its replacement by a tumour-specific or tissue-specific promoter and thus the production of one of the nucleic acids according to the present invention, ensures that genes and gene products that are important for adenoviral replication are under the control of the tumour or of the corresponding tissue and consequently replication of the adenovirus occurs specifically in the tumour or in a particular tissue. This meets the requirement for a specific virus-mediated lysis of cells and thus ensures the safety of the system. In this connection the E2 late promoter can be inactivated by being completely deleted. However, it is also possible within the scope of the invention for the E2 late promoter to be changed in such a manner that it is no longer functionally active as a promoter. This can for example be carried out by changing, e.g. mutating or deleting, the binding site of the promoter for YB-1 in such a manner that YB-1 can no longer bind to the promoter. The deletion of the Y box from the promoter is an example of such a deletion. The term used herein that a nucleic acid according to the present invention comprises a tissue-specific or tumour-specific promoter instead of the E2 promoter encompasses the methods described above. To this extent the term is to be understood in a functional manner.

In order to further improve the safety of the system which controls the expression of the E2 gene products via a tumour-specific or tissue-specific promoter, in a preferred embodiment the E2 early promoter should be functionally inactive at the same time as the E2 late promoter, for example deleted or altered in such a manner that it is no longer functionally active as a promoter. This ensures that the E2 early promoter has no influence on the expression of the E2 genes. Instead the two promoters, i.e. the E2 late promoter and the E2 early promoter, are preferably replaced by a tissue-specific or tumour-specific promoter according to the present invention. Also in this case the promoters described herein in connection with the YB-1 encoding nucleic acid sequences can be used.

The adenoviral nucleic acid or the corresponding adenoviruses preferably comprise the genes for E1A, E1B, E2 and E3. In preferred embodiments the nucleic acid coding for E3 can be deleted.

The adenovirus constructs described above and in particular their nucleic acids can also be introduced in parts into a cell, in particular a tumour cell, in which case they interact due to the presence of the various individual components in such a manner as if the individual components were derived from an individual nucleic acid. A typical example of this which is referred to herein as an adenoviral replication system, provides that the adenoviral nucleic acid is deficient for the expression of the E1A protein. The preferably cellular replication system comprises a nucleic acid of a helper virus, whereby the nucleic acid of the helper virus contains a nucleic acid sequence which codes for YB-1. In this connection the adenoviral nucleic acid or the nucleic acid of the helper virus may be present individually or separately as replicable vectors.

The nucleic acids according to the present invention can be present as vectors. They are preferably viral vectors. In the case of the nucleic acids according to the present invention comprising adenoviral nucleic acids, the virus particle is in this case the vector. However, it is also within the scope of the present invention that the nucleic acids according to the present invention are present in a plasmid vector. In such a case the vector has elements which are responsible for or control the multiplication of the inserted nucleic acid (replication) and optionally the expression of the inserted nucleic acid. Suitable vectors and especially also expression vectors and elements are known to persons skilled in the art and are described for example in Grunhaus, A., Horwitz, M. S., 1994, Adenoviruses as cloning vectors. In Rice, C., editor, Seminars in virology, London: Saunders Scientific Publications, 1992; 237-252.

The embodiment described above in which the various elements of the nucleic acid according to the invention do not necessarily have to be contained in only one vector, takes into account the aspect of the invention which comprises the group of vectors. Correspondingly a group of vectors consists of at least two vectors. Otherwise the same applies to the vectors as has generally been stated herein with regard to vectors.

The adenoviruses according to the present invention are characterized by the various nucleic acids disclosed herein and otherwise contain all elements known to persons skilled in the field which is also the case for adenoviruses of the wild-type (Shenk, T.: Adenoviridae: The virus and their replication. Fields Virology, 3$^{rd}$ edition, editor Fields, B. N., Knipe, D. M., Howley, P. M. et al., Lippincott-Raven Publishers, Philadelphia, 1996, chapter 67).

The agents according to the present invention, i.e. the nucleic acids, and vectors and groups of vectors, cells and adenoviruses and adenoviral replication systems comprising the nucleic acids can be used for the manufacture of a medicament. As a result of the specific activities of the agents according to the present invention the medicament is preferably used as such for the treatment or prophylaxis of tumour diseases. These agents are basically suitable for all tumour diseases or tumours, and in particular also for tumours which contain p53 and those in which p53 is absent. The term tumour encompasses both malignant and benign tumours.

The medicament can be present in various formulations, preferably in a liquid form. The medicament also contains auxiliary substances such as stabilizers, buffers, preservatives and such like which are known to a person skilled in the field of galenics.

In particular the medicament can also contain other pharmaceutically active compounds. The type and the amount of these other pharmaceutically active compounds will depend on the type of indication for which the medicament is used. If the medicament is used for the treatment and/or prophylaxis of tumour diseases, cytostatic agents are typically used such as cis-platinum and Taxol, Daunoblastin, Adriamycin and/or Mitoxantron.

The use of attenuated adenoviruses such as Onyx-015 which is deficient in the E1B-55 kDa protein, has relatively little chance of success when used for viral oncolysis. The present inventor has surprisingly found that these attenuated viruses and especially also Onyx-015 can be used with a particularly high rate of success for tumours in which YB-1 occurs in the cell nucleus independent of the cell cycle. YB-1 is normally present in the cytoplasm and especially also in the perinuclear plasma. In the S phase of the cell cycle, YB-1 is located in the cell nucleus of normal and tumour cells. However, this is not sufficient to achieve a viral oncolysis using attenuated adenoviruses. The comparatively low effectiveness of attenuated adenoviruses such as Onyx-015 described in the prior art is also due to its erroneous application. In other words such systems and especially also Onyx-015 can be used very effectively when the molecular biological prerequisites for viral oncolysis are present. In the case of especially Onyx-015 these prerequisites are present in tumour diseases in which the cells have a nuclear localisation of YB-1 independent of the cell cycle. This form of nuclear localisation may be due to the type of the tumour or may be caused by the agents according to the invention described herein. Hence the present invention defines a new group of tumours or tumour diseases and thus also of patients which can be treated with a high rate of success with the agents according to the present invention and especially also with the attenuated adenovirus that has already been described in the prior art and preferably with E1B-deficient, more preferably E1B-55 kDa-deficient adenovirus and more preferably with Onyx-015.

Another group of patients that can be treated by using the adenoviruses described in the prior art and especially those that are deficient in E1B such as ONYX-015, are those in which it is ensured that YB-1 migrates or is transported into the nucleus by setting up certain conditions. The use of such adenoviruses in this group of patients is thus based on the finding that the induction of viral replication is based on the nuclear localisation of YB-1 with subsequent binding to the E2 late promoter. The findings disclosed herein show that the adenovirus ONYX-015 which is E1B-deficient, is not able to mediate transport of the cellular YB-1 into the nucleus. This is the reason for the limited use and success of ONYX-015 for such tumours which already have YB-1 in the nucleus. However, this is only the case for a very small group of patients. The localization of YB-1 in the nucleus can be induced by external stress or locally applied stress. This induction can for example be achieved by irradiation, in particular UV irradiation, and administration of cytostatic agents which have among others also been disclosed herein, and hyperthermia. In connection with hyperthermia, it should be noted that this can now be achieved very specifically and thus the transport of YB-1 into the nucleus is also specific and consequently the requirements for replication of the adenovirus and thus for cell and tumour lysis are fulfilled (Stein U, Jurchott K, Walther W., Bergmann S. Schlag P M, Royer H D. Hyperthermia-induced nuclear translocation of transcription factor YB-1 leads to enhanced expression of multidrug resistance-related ABC transporters. J. Biol. Chem. 2001, 276(30): 28562-9; Hu Z, Jin S, Scotto K W. Transcriptional activation of the MDR1 gene by UV irradiation. Role of NF-Y and Sp1. J. Biol. Chem. Jan. 28, 2000; 275(4): 2979-85; Ohga T, Uchiumi T, Makino Y, Koike K, Wada M, Kuwano M, Kohno K. Direct involvement of the Y box binding protein YB-1 in genotoxic stress-induced activation of the human multidrug resistance 1 gene. J. Biol. Chem. 1998, 273(11): 5997-6000).

Hence the medicament according to the present invention would be administered to such patients and groups of patients and would also be suitable for those in which transport of YB-1, especially in the corresponding tumour cells, would be induced by suitable pretreatments.

Thus another aspect of the invention is also related to a method for the screening of patients that can be treated with an attenuated adenovirus such as Onyx-015 or in general with E1B-deficient, preferably E1B-55 kDa-deficient adenovirus characterized by the following steps:
examining a sample of the tumour tissue and
determining whether YB-1 is located in the nucleus independent of the cell cycle.

In this connection the sample of the tumour tissue can be obtained by puncture or by surgery. Microscopic techniques and/or immunohistoanalysis typically using antibodies are frequently used to determine whether YB-1 is located in the nucleus independent of the cell cycle. YB-1 is detected using an agent which is selected from the group comprising antibodies against YB-1. The test for the nuclear localization of YB-1 and in particular independently of the cell cycle is known to a person skilled in the art. For example the localization of YB-1 can be easily detected when screening tissue sections stained for YB-1. In this case the frequency of the occurrence of YB-1 in the nucleus already indicates that it is a cell cycle-independent localization in the nucleus. Another method for the cell cycle-independent detection of YB-1 in the nucleus is to stain for YB-1 and determine whether YB-1 is located in the nucleus and to determine the cell stage of the cells. This can also be carried out using suitable antibodies (double immunohistoanalysis).

The invention is further elucidated in the following on the basis of the figures and examples from which further features, embodiments, applications and advantages may be taken.

Figure 2:
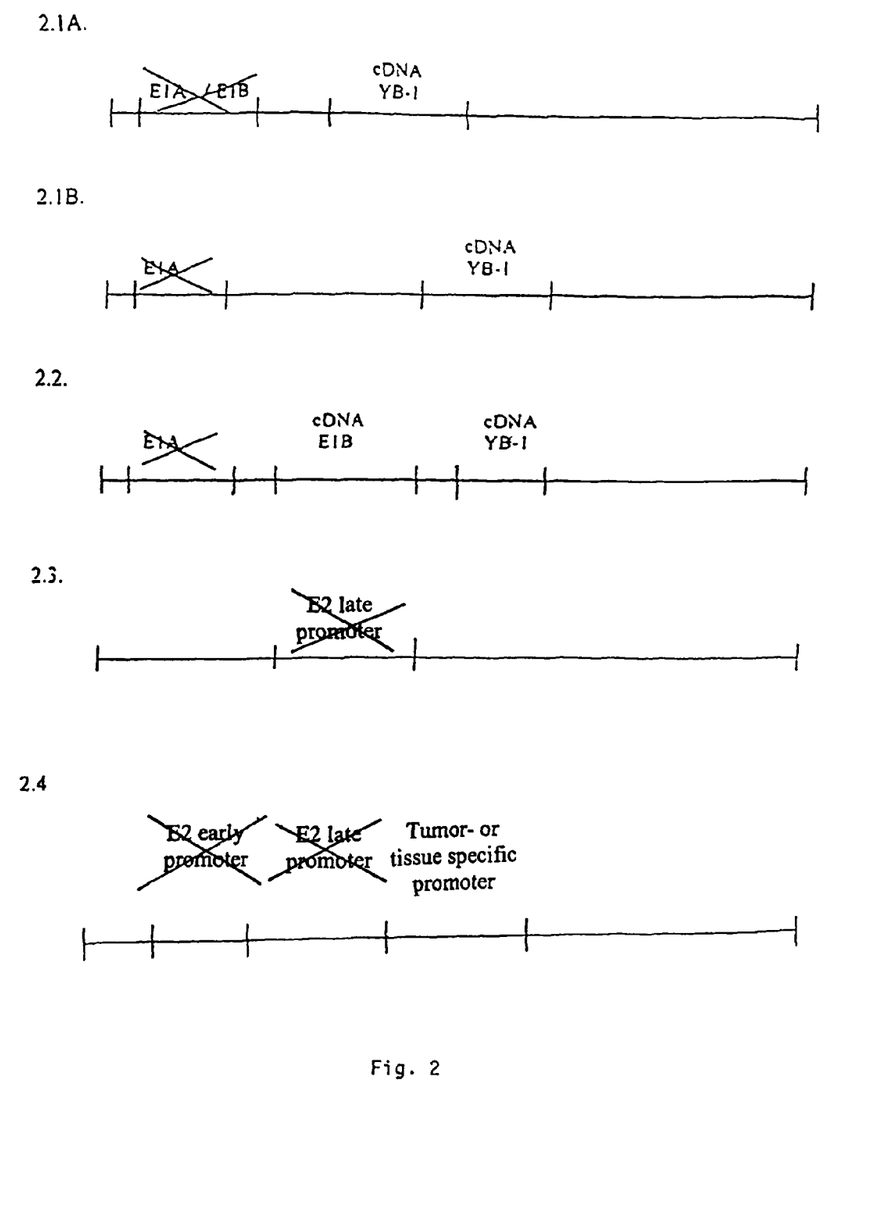
FIG. 2 shows an overview of various nucleic acid and adenovirus constructs according to the present invention and FIG. 3 shows the result of a Northern Blot analysis.
Figure 3:
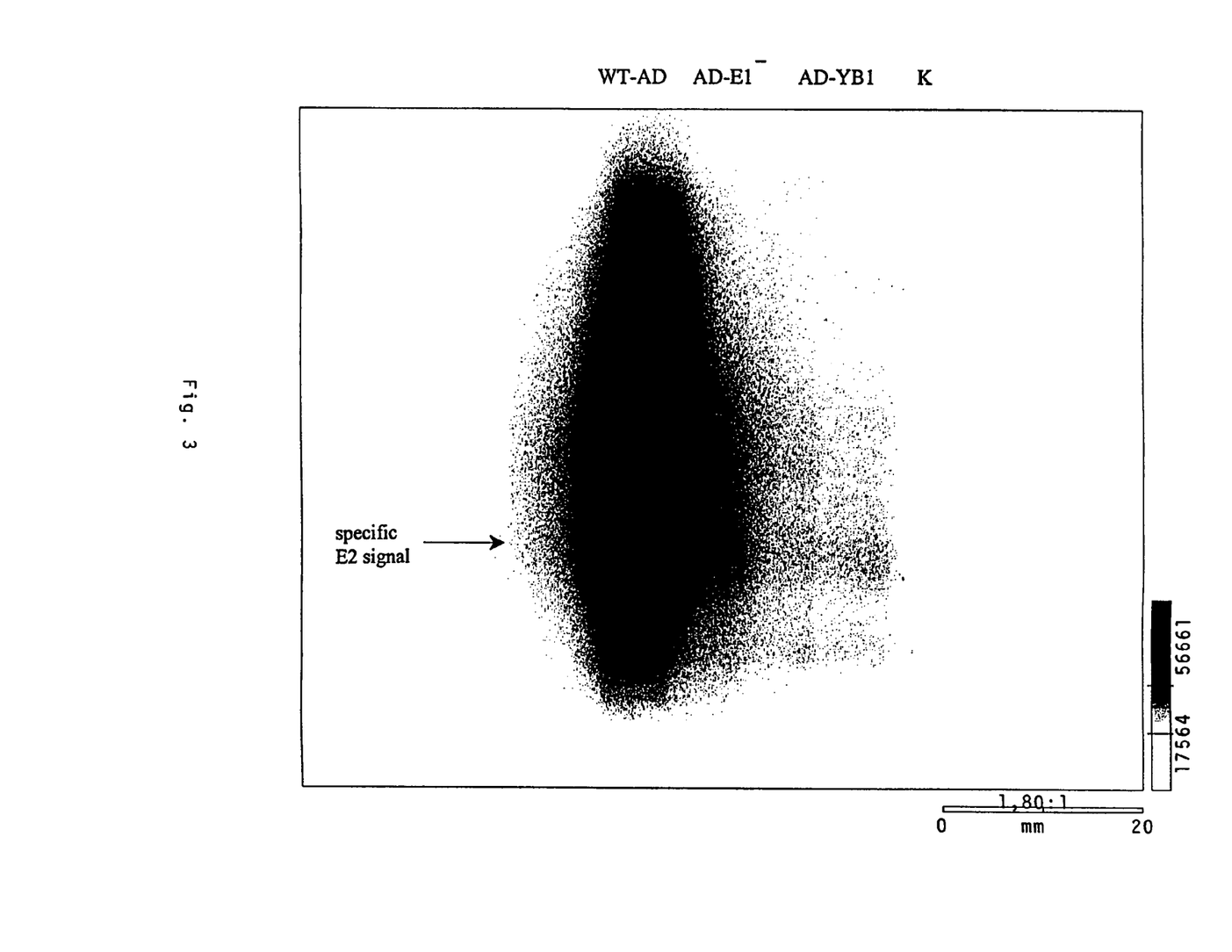

FIG. 2 shows different nucleic acids and nucleic acid constructs according to the present invention. Thus FIG. 2.1A shows a recombinant adenoviral vector according to the present invention which is E1A-deficient and E1B-deficient but expresses the protein YB-1.

FIG. 2.1B shows a recombinant adenoviral vector according to the present invention which also expresses YB-1 but in which the E1A region is deleted. Since E1A is responsible for the expression of E1B, E1B is not activated or only to a reduced extent although the vector comprises the gene.

FIG. 2.2 shows a recombinant adenoviral vector according to the present invention which also expresses YB-1. In this case the gene E1B and E1B-55 kDa, respectively, is controlled by an external E1A-independent promoter. Such a promoter can be the CMV, RSV or YB-1 promoter.

FIG. 2.3 shows another recombinant adenoviral vector according to the present invention which has a YB-1-independent E2 late promoter. This is achieved by completely removing the E2 late promoter or by specifically changing the gene sequence within the promoter to which YB-1 binds (the so-called Y box).

FIG. 2.4 shows another recombinant adenoviral vector according to the present invention in which the E2 late as well as the E2 early promoter are deleted and are thus no longer functionally active. In the vector shown schematically the two promoters are replaced by a tumour-specific or tissue-specific promoter as disclosed herein.

EXAMPLE 1

Importance of YB-1 for Adenoviral Replication

In order to prove that YB-1 controls the expression of E2 via the E2 late promoter the following experimental approach was pursued.

Tumour cells (HeLa cells) were either infected with wild-type adenovirus, an E1-minus adenovirus or with an E1-minus adenovirus which expresses YB-1 (AdYB-1) (in this connection K represents the control; non infected). The entire RNA was isolated after 24 h. Subsequently a Northern blot analysis was carried out. The isolated RNA was then separated according to size by gel electrophoresis in a formaldehyde-agarose gel and blotted on a nylon membrane and fixed under UV. A cDNA fragment of 250 bases which is complementary to a sequence which is located between the E2 early promoter and the E2 late promoter was used as a radioactively labelled probe. The probe was labelled with the aid of the random prime labeling system from Amersham. An analysis of the films showed that an E2-specific signal is only present in cells infected with the wild-type adenovirus.

EXAMPLE 2

Importance of YB-1 for Adenoviral Replication

In order to prove that YB-1 controls the expression of E2 via the E2 late promoter the following experimental approach was pursued which is based on the protocol described in example 1.

The radioactive probe of example 1 was removed by boiling for 2 minutes in water and again hybridized with another cDNA probe. This probe is located upstream of the E2 late promoter.

The analysis gave the following result: The cells infected with wild-type adenovirus as well as the cells infected with AdYB-1 have a clear signal and a specific E2 band. Hence YB-1 controls and activates the E2 region via the E2 late promoter.

EXAMPLE 3

Proof of the Specific Binding of YB-1 to the E2 Promoter

The experiment is based on the consideration that YB-1 as a transcription factor should bind to the Y box (CAAT sequence) within the E2 late promoter. In order to detect such a specific binding of YB-1 to this promoter, a so-called EMSA analysis (electrophoretic mobility shift assay) is carried out. For this the nuclear protein is isolated 24 h after infecting the cells with wild-type adenovirus. Subsequently 1-10 μg protein and a short DNA fragment with a length of 30 to 80 bases which comprises the E2 late promoter sequence are incubated together for 30 minutes at 37° C. This DNA fragment (oligo) is previously radioactively labelled with $^{32}P$ at the 5' end using a kinase. Afterwards a native polyacrylamide gel is used for separation. If the protein YB-1 binds to a sequence on the oligo, a so-called shift results since the short DNA fragment, which is radioactively labelled at the 5' end, migrates in the gel due to the binding of YB-1 to the short DNA fragment more slowly than an unbound oligo. This shift can be abolished again as soon as a 100-fold excess of non-labelled oligo is added to the reaction mixture.

As a result it has been determined that YB-1 binds specifically to the E2 late promoter.

Competition experiments were carried out as a control. An excess of non-labelled E2 late promoter fragment was added to the reaction mixture. Subsequently a shift is no longer observed in the above reaction mixture.

If reference is made to the prior art in the above description, it or its disclosed contents are incorporated herein by way of reference.

The features of the invention disclosed in the previous description, the claims and the figures can be important individually as well as in any desired combination for the realization of the invention in its various embodiments.

The invention claimed is:

1. A nucleic acid comprising an adenovirus sequence encoding a replicating adenovirus and further comprising a YB-1 coding sequence operably linked to an expression control sequence.

2. The nucleic acid of claim 1, wherein the adenovirus sequence comprises a nucleic acid coding for an E1-B 55 kDa protein.

3. The nucleic acid of claim 1, wherein the adenovirus sequence comprises a nucleic acid coding for E4orf6.

4. The nucleic acid of claim 1, wherein the expression control sequence comprises a promoter.

5. The nucleic acid of claim 1, wherein the adenovirus sequence comprises a nucleic acid coding for an E1B, an E1, an E3 or an E4 protein, or any combination thereof.

6. A vector, preferably an expression vector, comprising the nucleic acid of claim 1.

7. An adenovirus comprising the nucleic acid of claim 1.

* * * * *